United States Patent
Hirata et al.

(10) Patent No.: US 8,128,789 B2
(45) Date of Patent: *Mar. 6, 2012

(54) METHOD FOR PRODUCING ULTRAFINE DISPERSION WATER OF NOBLE METAL ULTRAFINE PARTICLES

(75) Inventors: Yoshihiro Hirata, Kyoto (JP); Yoshio Ueda, Kyoto (JP); Hiroaki Takase, Kyoto (JP); Kazuaki Suzuki, Kyoto (JP)

(73) Assignee: Phiten Co., Ltd., Kyoto-shi (JP)

( * ) Notice: Subject to any disclaimer, the term of this patent is extended or adjusted under 35 U.S.C. 154(b) by 1196 days.

This patent is subject to a terminal disclaimer.

(21) Appl. No.: 11/862,048

(22) Filed: Sep. 26, 2007

(65) Prior Publication Data

US 2008/0011614 A1    Jan. 17, 2008

Related U.S. Application Data

(62) Division of application No. 10/492,333, filed as application No. PCT/JP02/10566 on Oct. 11, 2002, now abandoned.

(30) Foreign Application Priority Data

Oct. 12, 2001  (JP) .................................. 2001-315205
Oct. 12, 2001  (JP) .................................. 2001-315257

(51) Int. Cl.
  *B22F 9/14*  (2006.01)
(52) U.S. Cl. ..................... 204/164; 422/186.04; 75/345; 75/346
(58) Field of Classification Search .................. 204/164; 422/186.04

See application file for complete search history.

(56) References Cited

U.S. PATENT DOCUMENTS

| | | |
|---|---|---|
| 3,171,813 A | 3/1965 | Inoue |
| 4,731,515 A | 3/1988 | Savage et al. |
| 4,967,958 A * | 11/1990 | Helsper et al. ................. 239/81 |
| 5,587,170 A | 12/1996 | Caisey et al. |
| 5,707,419 A | 1/1998 | Tsantrizos et al. |
| 5,879,518 A | 3/1999 | Kuehnle |
| 5,932,251 A | 8/1999 | Kirkpatrick |

(Continued)

FOREIGN PATENT DOCUMENTS

EP    1 238 946 A1    9/2002

(Continued)

OTHER PUBLICATIONS

Ripperger, Engineering Aspects and Applications of Crossflow Microfiltration, (1988), Chem. Eng. Technol. 11 pp. 17-25.*

(Continued)

*Primary Examiner* — Arun S Phasge
(74) *Attorney, Agent, or Firm* — Knobbe Martens Olson & Bear LLP

(57) ABSTRACT

Efficiently produce micro-dispersion water of super-fine noble metal particles having a desired concentration by using a very safe, compact production apparatus comprising a power supply for high-voltage/current discharge, a high-voltage discharge generator equipped with a noble metal electrode and its counter electrode, a water tank, a water inlet to the water tank, and an outlet for micro-dispersion water of super-fine noble metal particles, by causing plasma discharge in water between the noble metal electrode and its counter electrode and then causing the generated noble metal ion vapor to contact, and micro-disperse in, water. The obtained water can be effectively used as drinking water.

15 Claims, 2 Drawing Sheets

Production Flow Chart for Suspension Water of Super-Fine Noble Metal Particles

U.S. PATENT DOCUMENTS

| | | | |
|---|---|---|---|
| 6,103,272 A | 8/2000 | Keeney | |
| 7,108,735 B2 | 9/2006 | Hirata et al. | |
| 7,128,816 B2 * | 10/2006 | Denes et al. | 204/164 |
| 7,300,491 B2 * | 11/2007 | Hirata et al. | 75/346 |
| 2004/0231461 A1 | 11/2004 | Hirata et al. | |
| 2004/0237716 A1 | 12/2004 | Hirata et al. | |
| 2005/0019289 A1 | 1/2005 | Hirata et al. | |
| 2005/0042296 A1 | 2/2005 | Hirata et al. | |
| 2005/0092132 A1 | 5/2005 | Hirata et al. | |

FOREIGN PATENT DOCUMENTS

| | | |
|---|---|---|
| EP | 1 374 836 A1 | 1/2004 |
| EP | 1 393 841 A1 | 3/2004 |
| JP | 37-15016 | 9/1962 |
| JP | 63-089405 | 4/1988 |
| JP | 63-267431 | 11/1988 |
| JP | 02-166202 | 6/1990 |
| JP | 04-122433 | 4/1992 |
| JP | 05-339142 | 12/1993 |
| JP | 06-093311 | 4/1994 |
| JP | 06-510747 | 12/1994 |
| JP | 07-024305 | 1/1995 |
| JP | 09-010772 | 1/1997 |
| JP | 09-220580 | 8/1997 |
| JP | 11-228141 | 8/1999 |
| JP | 2000-340379 | 12/2000 |
| JP | 2001-048758 | 2/2001 |
| JP | 2001-137866 | 5/2001 |
| JP | 2001-314878 | 11/2001 |
| WO | WO 01/36337 A1 | 5/2001 |
| WO | WO 03/32932 A1 | 4/2003 |
| WO | WO 03/33417 A1 | 4/2003 |

OTHER PUBLICATIONS

The Office Action mailed on Jun. 20, 2007 issued in U.S. Appl. No. 10/493,903, filed Nov. 18, 2004.

T. Satsuta, et al., "Preparation of metal powders utilizing electric discharge in water," J of the Japan Institute of Metals, vol. 57, No. 6, 1993, pp. 692-698.

* cited by examiner

Fig. 1

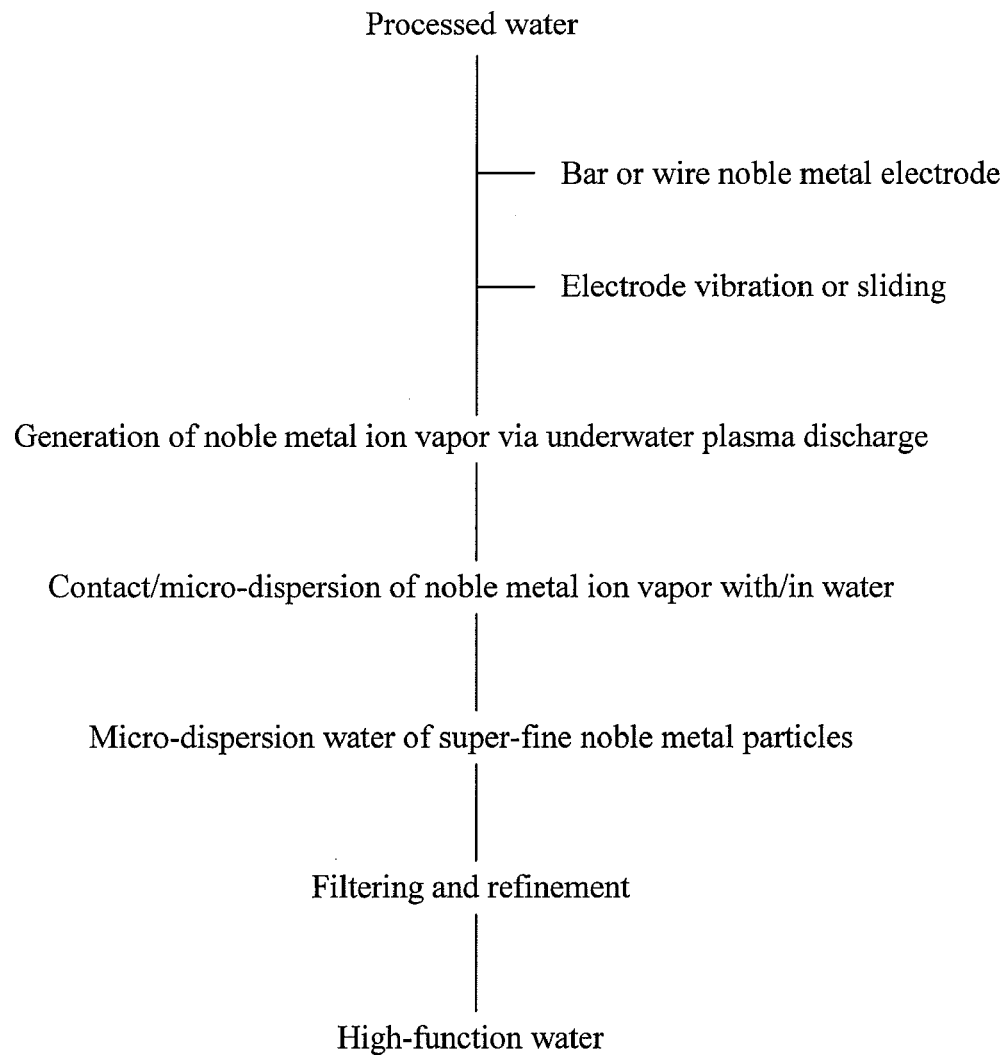

Production Flow Chart for Suspension Water of Super-Fine Noble Metal Particles

Processed water

— Bar or wire noble metal electrode

— Electrode vibration or sliding

Generation of noble metal ion vapor via underwater plasma discharge

Contact/micro-dispersion of noble metal ion vapor with/in water

Micro-dispersion water of super-fine noble metal particles

Filtering and refinement

High-function water

METHOD FOR PRODUCING ULTRAFINE DISPERSION WATER OF NOBLE METAL ULTRAFINE PARTICLES

CROSS-REFERENCE TO RELATED APPLICATIONS

This is a divisional application of U.S. patent application Ser. No. 10/492,333, filed Jun. 22, 2004, which is the U.S. National Phase under 35 U.S.C. §371 of International Application PCT/JP02/10566, filed on Oct. 11, 2002, which claims priority to Japanese Patent Application No. 2001-315205 filed on Oct. 12, 2001 and Japanese Patent Application No. 2001-315257 filed on Oct. 12, 2001. The disclosure of the U.S. patent application is herein incorporated by reference in its entirety. The International Application was published under PCT Article 21(2) in a language other than English.

FIELD OF THE INVENTION

This invention relates to a method and apparatus for efficiently producing micro-dispersion water of super-fine noble metal particles.

The invention also relates to healthy drinking water or cosmetic lotion that applies the obtained noble metal micro-dispersion water.

DESCRIPTION OF THE RELATED ART

Gold, platinum and silver have been considered some of the most valuable noble metals available to men since the ancient times and used chiefly in ornaments and treasures. However, the efficacies of these metals in the promotion of human health have also been recognized of late, and noble metals are now used in such applications as health bracelets made of pure gold or silver or Japanese sake containing gold foil.

In recent years, the health functions of noble metals have been again drawing the attention of the increasingly health-conscious public. In particular, noble metals in ion or fine particle form are now known to offer more remarkable health-promoting function than noble metals themselves or in flake form, such as gold foil.

The potential health-promoting function and disease-curing effect of noble metal ions and fine noble metal particles are generating strong interests. The significant contributions of noble metals to health are also known (*"Gold Water" Cured Intractable Diseases the Doctors Gave Up Treating*, written by Tonpu Takada), and future technological developments in this field are eagerly awaited. Currently, use of aqueous solution or water dispersion of noble metal ions and fine noble metal particles is considered feasible. However, there are several problems that must be solved before these applications can be put to commercial use.

As explained above, water that contains gold is already of public knowledge (p. 64 of the aforementioned book). However, most of the technologies for producing such water are based on simple dispersion of gold foil or powder in water. Dissolving gold ions or fine gold particles in water is very difficult, and the only methods known to date are limited to those that use aqua regia or gold electrolyte.

However, these conventional methods required high production costs and therefore did not provide desired economy. In addition, they also posed technical problems, such as unverified safety of using the obtained products for the purpose of promoting health.

The published technologies relating to the use of aqueous solution or water dispersion of noble metal ions and fine noble metal particles include the technology to mix with polyolefin molding resin an inorganic antibacterial agent produced by fixing to zeolite ion-exchange material gold ions and ions of other metals offering antibacterial function, in order to provide an antibacterial beverage tank that can protect the drink from bacteriophages permeating through the walls of the polyethylene beverage tank while keeping the original flavor of the drink (Registered Japanese Utility Model No. 3046284), the technology to release minerals into water by placing mineral carriers in water and then stimulating these carriers via stimulation means for releasing minerals, such as addition of acid or electrolysis, in order to provide mineral water that contains gold ions and other minerals beneficial to human body (Japanese Patent Application Laid-open No. 9-220580), the technology to micro-disperse heavy metals such as gold in acid ion water of pH 2.6 to 4.5 or oxidation potential water of pH 2.7 or less, both generated using an electrolytic water purifier, in order to produce sterilizing antiseptic water that offers excellent sterilization effect at low cost (Japanese Patent Application Laid-open No. 9-10772), and the technology to produce ice by uniformly agitating and mixing fold foil in crushed ice granules, filling the ice granules containing gold foil in an ice-making drum, and then gradually introducing water from the bottom of the ice-making drum to create ice, in order to produce healthy ice in which gold foil or other substance is uniformly distributed throughout the block of ice (Japanese Patent Application Laid-open No. 5-280841).

However, none of these conventional technologies offer fundamental solutions to the aforementioned problems, except for the technology to release minerals into water by placing mineral carriers in water and then stimulating these carriers via stimulation means for releasing minerals, such as addition of acid or electrolysis, in order to provide mineral water that contains gold ions and other minerals beneficial to human body (Japanese Patent Application Laid-open No. 9-10772), which offers potential.

In light of the above circumstance, the inventors developed the present invention after diligently studying ways to produce healthy water containing super-fine noble metal particles, based on the assumption that providing drinking water containing such noble metal ions and fine noble metal particles would embody an easy way to improve health and thereby enable improvement of various conditions.

DISCLOSURE OF THE INVENTION

As explained above, noble metal ions and fine noble metal particles offer potentially high health-promoting function and disease-curing effect. The modes of applying noble metals for these purposes include aqueous solution or water dispersion of noble metal ions and fine noble metal particles, but the conventional methods required high production costs and therefore did not provide desired economy. These methods also posed technical problems that remain unresolved, such as the insufficient health-promoting effects of the products and unverified safety of using chemical electrolytes in the human body.

Therefore, although use of noble metal ions and fine noble metal particles in bioactive materials, health food materials, cosmetics, drugs, etc., is expected to create huge demand, the specific technologies developed to date are not of satisfactory nature.

In view of the above situation, the present invention aims to solve these problems by creating micro-dispersion water of noble metal ions and fine noble metal particles and allowing the obtained water to be utilized in health-promoting applications such as bioactive materials, health food materials, cosmetics and drugs.

The present invention is a development of a new method and apparatus for producing micro-dispersion water of super-fine noble metal particles. Basically, the present invention allows for production of micro-dispersion water of super-fine noble metal particles by causing plasma discharge in water between an electrode made of noble metal and its counter electrode equipped on a high-voltage discharge generator and then causing the generated noble metal ion vapor to contact, and micro-disperse in, water. The trial tests of the obtained micro-dispersion water of super-fine noble metal particles confirmed that the water exhibited remarkable effects in improving physical condition and relieving fatigue, among others, and could be effectively used as drinking water.

In the context of the present invention, micro-dispersion water of super-fine noble metal particles refers to water in which very fine particles of noble metal are micro-dispersed, unlike other types of water in which noble metal powder or foil is simply floating.

Basically the present invention comprises of (1) through (7) below:

(1) A method for producing micro-dispersion water of super-fine noble metal particles by causing plasma discharge in water between an electrode made of noble metal and its counter electrode equipped on a high-voltage discharge generator and then causing the generated noble metal ion vapor to contact, and micro-disperse in, water.

(2) An apparatus for producing micro-dispersion water of super-fine noble metal particles, comprising a power supply for high-voltage/current discharge, a high-voltage discharge generator equipped with a noble metal electrode and its counter electrode, a water tank, a water inlet to the water tank, an outlet for produced water, and a discharge pump.

(3) An apparatus for producing micro-dispersion water of super-fine noble metal particles as described in (2), wherein the noble metal electrode has a bar or wire shape and a device to successively feed the electrode is provided.

(4) An apparatus for producing micro-dispersion water of super-fine noble metal particles as described in (2) or (3), wherein a device for vibrating or sliding in the water tank the noble metal electrode and its counter electrode equipped on the high-voltage discharge generator is attached as an adjunct.

(5) An apparatus for producing micro-dispersion water of super-fine noble metal particles as described in any one of (2) through (4), wherein a filter system for removing the generated coarse noble metal particles is attached as an adjunct.

(6) An apparatus for producing micro-dispersion water of super-fine noble metal particles as described in any one of (2) through (5), wherein the residue of fine noble metal particles left on the filter system is backwashed in the filter system and recovered.

(7) Micro-dispersion water of super-fine noble metal particles obtained by causing plasma discharge in water between an electrode made of noble metal and its counter electrode equipped on a high-voltage discharge generator and then causing the generated noble metal ion vapor to contact, and micro-disperse in, water.

(8) Micro-dispersion water of super-fine noble metal particles as described in (7), wherein the water is healthy drinking water, health-promoting agent or cosmetic lotion.

(9) Micro-dispersion water as described in (7) or (8), wherein the noble metal is gold.

BRIEF DESCRIPTION OF THE DRAWINGS

"FIG. 1"
A flow chart outlining the process proposed by the present invention
"FIG. 2"
An apparatus for producing micro-dispersion water of super-fine noble metal particles as proposed by the present invention

DESCRIPTION OF THE SYMBOLS

Figure 2:
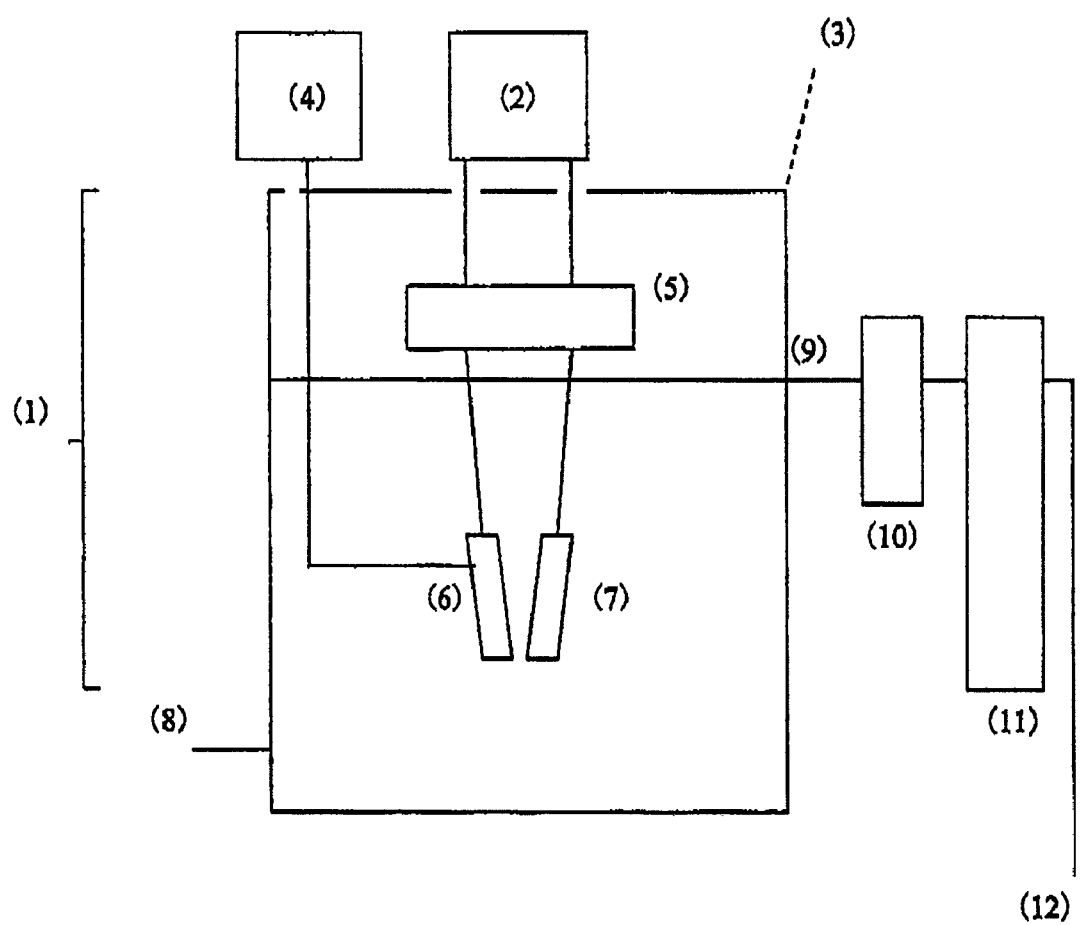

1: High-voltage discharge generator
2: Power supply for high-voltage/current discharge
3: Water tank
4: Electrode feeder
5: Electrode-vibrating/sliding device
6: Noble metal electrode
7: Counter electrode
8: Water inlet to the water tank
9: Outlet for micro-dispersion water of super-fine noble metal particles
10: Discharge pump for micro-dispersion water of super-fine noble metal particles
11: Filter system
12: Product

BEST MODE FOR CARRYING OUT THE INVENTION

Of noble metals, gold and platinum particles do not dissolve or disperse in water. Therefore, even when a dispersed state of fine gold or platinum particles is somehow achieved in water, the surface area of particles is small relative to the weight of gold or platinum mixed into water, thus resulting in poor cost-efficiency. The dispersed particles will also settle quickly. Therefore, any method that achieves such temporary dispersion does not satisfy the technical requirements.

The inventors diligently studied ways to improve these conventional technologies for the purpose of producing micro-dispersion water of super-fine noble metal particles. Specifically, the present invention was developed as a technology to produce micro-dispersion water of super-fine noble metal particles by causing plasma discharge in water between an electrode made of noble metal and its counter electrode equipped on a high-voltage discharge generator and then causing the generated noble metal ion vapor to contact, and micro-disperse in, water, based on the assumption that micro-dispersing super-fine noble metal particles of micron to nano-scale, which are smaller than fine noble metal particles, would improve the various shortcomings mentioned above.

One feature of the present invention is that it has realized a production and utilization of water in which super-fine noble metal particles of micron to nano-order are micro-dispersed, which are finer than the normal fine noble metal particles as mentioned above. This way, stable micro-dispersion water in which super-fine noble metal particles remain dispersed without settling for a longer period of time compared with water in which flakes of noble metal foil or fine noble metal particles are simply floating. Its physical properties make the obtained water safe for human consumption just like normal water, and the water also provides high functions in promoting health, among others.

The primary feature of the present invention is that it provides a method to produce micro-dispersion water of super-fine noble metal particles by causing plasma discharge in water between an electrode made of noble metal and its counter electrode and then causing the generated noble metal ion vapor to contact, and micro-disperse in, water. This process is outlined in FIG. 1.

The basic production method proposed by the present invention is to continuously or intermittently feed water into the water tank and cause plasma discharge in water between an electrode made of noble metal and its counter electrode and thus heat the noble metal to high temperatures to generate noble metal vapor, and then cause the generated noble metal ion vapor to instantly contact water and micro-disperse in water. At this time, very small "super-fine" noble metal particles of micron to nano-scale are generated and micro-dispersed.

Here, fusing of the noble metal electrode can be prevented by vibrating or sliding in the water tank the noble metal electrode and its counter electrode equipped on the high-voltage discharge generator, and the amount of micro-dispersion can be controlled easily for generation of instant arc. Since the noble metal electrode will be consumed as super-fine particles, an electrode having a bar or wire shape is fed. Additionally, there is no need to select a different power supply for a given purpose, because the amount of current flowing through the circuit can be adjusted easily by changing the diameter and length of the counter electrode made of carbon, etc.

The produced water is retrieved from the outlet using the discharge pump and can be used directly without filtering. Depending on the application, filtering the water using a filter system, etc., will remove a trace amount of fine noble metal particles with a larger particle size and help yield micro-dispersion water in which only super-fine particles are micro-dispersed. The residue of fine noble metal particles left on the filter can be recovered by backwash and reused, as necessary, to improve economy.

The apparatus for producing noble metal micro-dispersion water proposed by the present invention, as illustrated in FIG. 2, provides an apparatus for producing micro-dispersion water in which super-fine noble metal particles are micro-dispersed, wherein the apparatus comprising a power supply for high-voltage/current discharge (2), a high-voltage discharge generator (1) equipped with a noble metal electrode (6) and its counter electrode (7), a water tank (3), a water inlet to the water tank (8), an outlet for produced micro-dispersion water of super-fine noble metal particles (9), and a discharge pump (10). An electrode feeder (4) that feeds the electrode pair on the high-voltage discharge generator, an electrode-vibrating/sliding device (5) that vibrates or slides the electrodes, and a filter system (11) for the obtained micro-dispersion water will be attached as adjuncts.

The production container used in the present invention comprising the water tank (3) made of metal, or preferably steel, wherein water is supplied from the inlet (8) and the noble metal electrode (6) and its counter electrode (7) on the high-voltage discharge generator (1) are submerged in water. By charging current between the electrodes in this condition, plasma discharge will occur and noble metal ions will instantly separate from the noble metal electrode and micro-disperse in water, thereby generating water in which super-fine noble metal particles are micro-dispersed.

When causing plasma discharge between the noble metal electrode and its counter electrode, vibrating or sliding both electrodes will prevent electrode fusion, and the amount of micro-dispersion can be controlled easily for generation of instant arc.

The obtained micro-dispersion water can be used directly, or fed by the discharge pump (10) to pass through the filter system (11) to obtain filtered product (12). A desirable filter system is one using hollow-fiber membranes of micron order mesh, instead of ion-exchange membranes or reverse-osmosis membranes, in order to filter only super-fine particles through.

Under the present invention, achievement of pulsed plasma discharge will allow for a near-continuous production of micro-dispersion water of super-fine noble metal particles, even when the production volume is increased. Since the apparatus can also be constructed in a small size, the present invention provides an efficient production method. The simple apparatus is also safe, because it does not require overly high pressure resistance.

If fine noble metal particles of relatively large size must be removed from the produced micro-dispersion water, it is desirable to attach a filter system (11) to this apparatus as an adjunct.

To refine the produced water for use as healthy drinking water or cosmetic lotion, pass it through a filter system (11) comprising hollow-fiber membranes of micron order mesh, as explained above, to remove the produced fine noble metal particles.

Filtering will provide drinking water meeting the food sanitation standards or cosmetic lotion meeting the cosmetics material standards. One example of filtration using hollow-fiber membrane filter is to provide hollow-fiber membranes of 50 microns, 25 microns, 3 microns, 0.5 micron and 0.1 micron at the point where the produced water is discharged from the reaction tank, and then let the water pass through these membranes sequentially. Filtered fine noble metal particles can be recovered via backwash and reused for added economy.

The high-function water obtained by the present invention can be used as healthy drinking water, health-promoting agent, cosmetics, food preservative, freshness-keeping agent for food, insecticide, deodorant, etc.

Although no theoretical explanations can be offered at the present as to why the high-function water obtained by the present invention can be effectively utilized in the above applications, as described later on the trial tests of sample water containing gold found remarkable improvements such as improved physical condition and relieved fatigue, thereby confirming the actual efficacies of such water.

Among other noble metals, gold is expected to offer excellent levels of stability, intestinal absorption and other physiological effects in the body, partly due to the ion-releasing effect and very large active surface area of its super-fine particles, and partly due to the unique characteristics and physiochemical stability of gold itself.

An example of the present invention is explained according to the drawings. Note, however, that the present invention is not limited to this example.

EXAMPLE

This example uses the apparatus shown in FIG. 2 for producing micro-dispersion water in which super-fine noble metal particles are micro-dispersed, comprising a 200-liter water tank (3), and a high-voltage discharge generator (1) equipped with a noble metal electrode (6) and its counter electrode (7).

A gold or platinum bar is used as the noble metal electrode, while the same metal or carbon is used as the counter electrode, and the two electrodes are charged with electricity for one hour. The electrodes may be fixed plates, or bars or wires that are successively fed using an auxiliary device. Either way, the electrodes are vibrated or slid by an electrode-vibrating/sliding device (5), and plasma discharge is caused in water between the noble metal electrode and its counter electrode by supplying power to the high-voltage discharge generator (1).

The production container is a pressure-resistant water tank (3) made of metal, or preferably steel, wherein water is fed through an inlet (8) and the noble metal ion vapor generated from the noble metal electrode via plasma discharge between the electrodes is caused to instantly contact, and micro-disperse in, water, in order to provide micro-dispersion water in which super-fine noble metal particles are micro-dispersed.

The produced noble metal micro-dispersion water is fed by a pump (10) through a filter system (11), as appropriate, to be obtained as product (12). The filter system uses hollow-fiber membranes of 50 microns, 25 microns, 3 microns, 0.5 micron and 0.1 micron, and the water is passed through these membranes sequentially.

The obtained micro-dispersion water was used in the trial tests as described below:

Trial Tests of Healthy Drinking Water

Ten adult males and females were instructed to drink healthy drinking water in which super-fine gold particles are micro-dispersed, and the health-promoting and disease-curing efficacies and effects of the water were verified.

Amounts Consumed and Conditions

| Amount of water consumed per day: | About 1 glass | 5 persons |
| --- | --- | --- |
| | Up to 3 glasses | 2 persons |
| | 4 glasses or more | 3 persons |
| Taste: | Tasty | 9 persons |
| | No taste | 1 person |
| Smell: | Not noticeable | 9 persons |
| | Noticeable | 1 person |

Verification of Efficacies

The numbers of persons among ten subjects who found that the water was effective are shown below.

This test involved a group of ten males and females different from the above subjects.

Table 1 shows the subjects' evaluations of the water provided by the present invention and the comparison water explained below.

As the comparison water, a water mixture of gold foil and fine gold particles with an average particle size of 1 mm was produced by a conventional technology and used (10 cc of this water contained 10 mg of gold).

TABLE 1

| Tested sample | Water by the present invention | Comparison example |
| --- | --- | --- |
| Improvement of physical condition | 8 | 3 |
| Relief of fatigue | 6 | 2 |
| Increase in appetite | 5 | 0 |
| Improvement of stomach condition | 7 | 0 |
| Drop in blood pressure | 3 | 0 |
| Healing of gastritis | 3 | 0 |
| Relief of eye fatigue | 2 | 0 |

The figures in Table 1 indicate degrees of effects based on a 10-point scale from very effective (10) to no effect (0).

As shown by the test results, most subjects answered that the beverage obtained by the present invention was easy to drink in terms of taste and smell. It was also found that the beverage had remarkable effects in the improvement of health functions, such as improvement of physical condition and increase in appetite.

In this example, a gold bar was used as electrode material to obtain the above high-function healthy drinking water in which super-fine gold particles are micro-dispersed. However, the high-function water produced with a bar electrode made of platinum, instead of gold, also exhibited the same effects.

INDUSTRIAL FIELD OF APPLICATION

As explained above, the present invention provides a new method and apparatus for producing micro-dispersion water of super-fine noble metal particles, as well as healthy drinking water utilizing this newly developed micro-dispersion water of super-fine noble metal particles. The compact apparatus reduces the capital investment, and its design allows for easy, low-cost production of micro-dispersion water of super-fine noble metal particles. When this micro-dispersion water of super-fine noble metal particles is used as drinking water or cosmetic lotion, such water/lotion will exhibit remarkable effects in the improvement of health functions, such as improvement of physical condition and increase in appetite, due to the bioactivity of super-fine noble metal particles.

What is claimed is:

1. A method for producing micro-dispersion water of super-fine noble metal particles comprising:
    generating instant arc discharge in water between an electrode made of noble metal and its counter electrode equipped on a high-voltage discharge generator to generate noble metal ion vapor while vibrating or sliding the noble electrode and the counter electrode against each other to inhibit the noble electrode and the counter electrode from being fused, said noble electrode and counter electrode being otherwise fused to each other; and
    causing the generated noble metal ion vapor to contact, and micro-disperse in, water, thereby producing micro-dispersion water of super-fine noble metal particles.

2. The method according to claim 1, wherein the noble meal electrode has a bar or wire shape, and the method further comprises successively feeding the noble metal electrode.

3. The method according to claim 1, wherein the instant arc discharge is pulsed discharge.

4. An apparatus for producing micro-dispersion water of super-fine noble metal particles, comprising a power supply for high-voltage/current discharge, a high-voltage discharge generator equipped with a noble metal electrode and its counter electrode, a water tank, a water inlet to the water tank, an outlet for produced water, a discharge pump, and a device for vibrating or sliding in the water tank the noble metal electrode and its counter electrode equipped on the high-voltage discharge generator to inhibit the noble metal electrode and the counter electrode from being fused to each other.

5. The apparatus for producing micro-dispersion water of super-fine noble metal particles as described in claim 4, wherein the noble metal electrode has a bar or wire shape and a device to successively feed the electrode is provided.

6. The apparatus for producing micro-dispersion water of super-fine noble metal particles as described in claim 5, further comprising a filter system for removing generated coarse noble metal particles.

7. The apparatus for producing micro-dispersion water of super-fine noble metal particles as described in claim 6, wherein the residue of fine noble metal particles left on the filter system is backwashed in the filter system and recovered.

8. The apparatus for producing micro-dispersion water of super-fine noble metal particles as described in claim 5, wherein the residue of fine noble metal particles left on the filter system is backwashed in the filter system and recovered.

9. The apparatus for producing micro-dispersion water of super-fine noble metal particles as described in claim 4, further comprising a filter system for removing generated coarse noble metal particles.

10. The apparatus for producing micro-dispersion water of super-fine noble metal particles as described in claim 9, wherein the residue of fine noble metal particles left on the filter system is backwashed in the filter system and recovered.

11. The apparatus for producing micro-dispersion water of super-fine noble metal particles as described in claim 4, wherein the residue of fine noble metal particles left on the filter system is backwashed in the filter system and recovered.

12. The apparatus according to claim 4, wherein the power supply is adapted to supply power in pulses.

13. A method for producing healthy drinking water or cosmetic lotion constituted of super-fine noble metal particles dispersed in water comprising:
    providing a apparatus comprising a power supply for high-voltage/current discharge, a high-voltage discharge generator equipped with a noble metal electrode and its counter electrode, a water tank, a water inlet to the water tank, an outlet for produced water, a discharge pump, a filter system, and a device for vibrating or sliding the noble metal electrode and its counter electrode equipped on the high-voltage discharge generator;
    feeding water into the water tank;
    generating instant arc discharge in the water between the noble metal electrode and the counter electrode equipped on the high-voltage discharge generator to generate noble metal ion vapor while vibrating or sliding the noble electrode and the counter electrode against each other to inhibit the noble electrode and the counter electrode from being fused, said noble electrode and counter electrode being otherwise fused to each other;
    causing the generated noble metal ion vapor to contact, and micro-disperse in, the water, thereby producing micro-dispersion water of super-fine noble metal particles; and
    filtering the micro-dispersion water through the filter system for removing coarse noble metal particles.

14. The method according to claim 13, wherein the noble metal electrode has a bar or wire shape and the apparatus further comprises a device to feed the electrode, thereby feeding the electrode successively.

15. The method according to claim 13 further comprising recovering and recycling the coarse noble metal particles left on the filter system by backwashing.

\* \* \* \* \*